United States Patent
Strauss et al.

(10) Patent No.: US 11,197,827 B2
(45) Date of Patent: Dec. 14, 2021

(54) POLYNUCLEOTIDE ENCAPSULATION AND PRESERVATION USING SELF-ASSEMBLING MEMBRANES

(71) Applicant: MICROSOFT TECHNOLOGY LICENSING, LLC, Redmond, WA (US)

(72) Inventors: Karin Strauss, Seattle, WA (US); Bichlien Hoang Nguyen, Seattle, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 320 days.

(21) Appl. No.: 16/177,188

(22) Filed: Oct. 31, 2018

(65) Prior Publication Data
US 2020/0129432 A1    Apr. 30, 2020

(51) Int. Cl.
| | |
|---|---|
| *A61K 9/127* | (2006.01) |
| *A61K 47/69* | (2017.01) |
| *A61K 47/62* | (2017.01) |
| *A61K 31/7088* | (2006.01) |
| *A61K 47/14* | (2017.01) |
| *A61K 47/18* | (2017.01) |
| *A61K 47/26* | (2006.01) |
| *A61K 47/36* | (2006.01) |

(52) U.S. Cl.
CPC .......... *A61K 9/1271* (2013.01); *A61K 9/1277* (2013.01); *A61K 31/7088* (2013.01); *A61K 47/14* (2013.01); *A61K 47/183* (2013.01); *A61K 47/26* (2013.01); *A61K 47/36* (2013.01); *A61K 47/62* (2017.08); *A61K 47/6911* (2017.08)

(58) Field of Classification Search
CPC .................................................... A61K 9/1271
See application file for complete search history.

(56) References Cited

U.S. PATENT DOCUMENTS

| | | |
|---|---|---|
| 2010/0285111 A1 | 11/2010 | Ko et al. |
| 2012/0201872 A1 | 8/2012 | Huang et al. |
| 2016/0138044 A1 | 5/2016 | Hayes et al. |

OTHER PUBLICATIONS

Bui et al. (J. Am. Chem. Soc. 2012, 134, 20189-20196) (Year: 2012).*
Bui et al. (J. Am. Chem. Soc. 2012, 134) Supporting Information for: Encapsidation of RNA-Polyelectrolyte Complexes with Amphiphilic Block Copolymers: Toward a New Self-Assembly Route (Year: 2012).*
Peterson et al. (WIREs Nanomed Nanobiotechnol 2015, 7:282-297. doi: 10.1002/wnan.1309) (Year: 2015).*
Church et al. (Next-generation digital information storage in DNA. Science 2012, 337:1628). (Year: 2012).*
Mark Davis (Current Opinion in Biotechnology 2002, 13:128-131). (Year: 2002).*
Bonnet, Jacques, et al., "Chain and conformation stability of solid-state DNA: implications for room temperature storage", In the Proceedings of Nucleic Acids Research, 2010, vol. 38, No. 5, Dec. 7, 2009, pp. 1531-1546.
Grass, Robert N., et al., "Robust Chemical Preservation of Digital Information on DNA in Silica with Error-Correcting Codes", In the Journal of Angewandte Chemie International Edition, vol. 54,No. 8, Feb. 4, 2015, 21 Pages.
Muller, David M., et al., "Engineering Protocells: Prospects for Self-Assembly and Nanoscale Production-Lines", In the Journal of Life, vol. 5, No. 2, Mar. 25, 2015, pp. 1019-1053.
Organick, Lee, et al., "Random access in large-scale DNA data storage", In the Journal of Nature biotechnology, vol. 36, No. 3, Feb. 19, 2018, pp. 242-250.
Pelta, Juan, et al., "DNA Aggregation Induced by Polyamines and Cobalthexamine", In the Journal of Biological Chemistry, vol. 271, No. 10, Dec. 20, 1995, pp. 5656-5662.
Viola, JR, et al., "Fatty acid-spermine conjugates as DNA carriers for nonviral in vivo gene delivery", In the Journal of Gene therapy, vol. 16, No. 12, Sep. 3, 2009, pp. 1429-1440.
Yin, Yudan, et al., "Non-equilibrium behaviour in coacervate-based protocells under electric-field-induced excitation", In Journal of Nature Communications, vol. 7, 2016, Feb. 15, 2016, 7 Pages.
Dewa, et al. "Liposomal Polyamine-Dialkyl Phosphate Conjugates as Effective Gene Carriers: Chemical Structure, Morphology, and Gene Transfer Activity", In Journal of Bioconjugate Chemistry, vol. 21, Issue 5, May 19, 2010, pp. 844-852.
Funhoff, et al., "PEG Shielded Polymeric Double-Layered Micelles for Gene Delivery", In Journal of Controlled Release, vol. 102, Issue 3, Feb. 16, 2005, pp. 711-724.
"International Search Report and Written Opinion Issued in PCT Application No. PCT/US2019/056417", dated Jan. 30, 2020, 18 Pages.
Zhang, et al., "Stabilized Plasmid-Lipid Particles for Regional Gene Therapy: Formulation and Transfection Properties", In Journal of Gene Therapy, vol. 6, Issue 8, Aug. 1999, pp. 1438-1447.

* cited by examiner

*Primary Examiner* — Scott Long
(74) *Attorney, Agent, or Firm* — Newport IP, LLC; Benjamin A. Keim (57) ABSTRACT

Polynucleotides such as DNA are stored inside vesicles formed from self-assembling membranes. The vesicles may be protocells, liposomes, micelles, colloidosomes, proteinosomes, or coacervates. The vesicles may include surface functionalization to improve polynucleotide encapsulation and/or to bind polynucleotides having specific sequences. Encapsulation in vesicles provides protection for the polynucleotides. Additional protection is provided by addition of one or more stabilizers. The stabilizer may be nucleic-acid stabilizers that stabilize the polynucleotides or may be a protective structural layer around the vesicles such as a layer of silica. A process for stably storing polynucleotides in vesicles and a process for recovering stored polynucleotides from vesicles are both disclosed. The polynucleotides may be used for storage of digital information.

12 Claims, 7 Drawing Sheets

Fluorescence microscope image of coacervate-DNA conjugates. White spots indicate the colocalization of DNA within coacervates. DNA is labeled with Cyanine5. Magnification 6.3x.

SCANNING ELECTRON MICROSCOPE IMAGE OF COACERVATES TREATED WITH TEOS FORMING A THIN FILM OF SILICON DIOXIDE. MAGNIFICATION IS 42,227X.

AGAROSE GEL SHOWING A 150 BP DNA BAND FOR COACERVATES PROTECTED WITH TEOS.

POLYNUCLEOTIDE ENCAPSULATION AND PRESERVATION USING SELF-ASSEMBLING MEMBRANES

BACKGROUND

The volume of digital information is increasing at an exponential rate. This vast increase in the amount of digital information may outpace the ability of conventional storage technologies. One promising technology for storing large amounts of digital information is deoxyribonucleic acid (DNA). DNA is well known as a molecule that can store genetic information. However, DNA can also function as a storage medium for digital information. Multiple different groups have successfully converted computer files into a string of nucleotide bases, synthesized DNA encoding that string, sequenced the synthetic DNA, and then recovered the original digital information with 100% accuracy.

As a storage medium, DNA has potential advantages over conventional optical and magnetic media in terms of information densities and stability. Storage using DNA can achieve a theoretical data density of over 200 petabytes (i.e., 200 million gigabytes) per gram which is much higher than possible with conventional media. With DNA it is possible that all the digital information in the world could be stored in a single room. DNA can also provide better long-term storage. Magnetic and optical media can wear out within five to 10 years. However, readable DNA has been recovered from fossils hundreds of thousands of years old.

Longevity of DNA, however, depends on storage conditions. DNA is susceptible to degradation by heat, enzymes, mutagenic chemicals, and ionizing radiation. When stored in solution DNA is stable for approximately 10 years, which is the same timescale as other storage media. Storage techniques that provide long-term stability and high data-density improve the usability of DNA as a storage medium for digital information.

SUMMARY

This disclosure provides structures and methods for stably storing nucleotides such as, but not limited to, DNA through encapsulation in self-assembling membranes. The polynucleotides to be stored are mixed with the precursors of a self-assembling vesicle. A vesicle is a closed structure formed by amphiphilic molecules (i.e., molecules with both hydrophilic or "water-loving" and lipophilic, "fat-loving" properties) and may contain a solvent and or other molecules inside the closed structure. When provided with appropriate conditions (e.g., pH, salt concentrations, etc.) the precursors spontaneously form spherical vesicles that contain the nucleotides. These spherical vesicles are small: typically on the scale of hundreds of nanometers to tens of micrometers ($1 \times 10^{-7}$ to $1 \times 10^{-5}$ meters). Types of vesicles that can be artificially formed with self-assembling membranes include protocells, liposomes, micelles, colloidosomes, proteinosomes, and coacervates.

Formation of vesicles in a solution that contains polynucleotides can result in the polynucleotides being pulled into the inside of the vesicles resulting in the concentration of polynucleotides inside the vesicles being much higher than the concentration in the surrounding solution. The vesicles' pore size, membrane permeability, interior functionalization, and exterior functionalization can concentrate either specific polynucleotides (i.e., preferentially moving polynucleotides having a certain nucleic acid sequence) or non-specific polynucleotides into the interior of the vesicle. Functionalization refers to the addition of specific chemical groups to the surface (interior or exterior) of the vesicle membrane.

Vesicles containing the polynucleotides are concentrated and dried. This removes all or substantially all of the solution and moisture. The dried vesicles may take the form of a powder. Thus, the polynucleotides are concentrated (relative to the concentration in solution) and protected by encapsulating in a self-assembling membrane. The polynucleotides are further protected by use of one or more stabilizers. The stabilizers protect the polynucleotides from damage and by doing so increase the length of time the polynucleotides can be stored without significant degradation.

Many different types of stabilizers may be used with the vesicle-encapsulated polynucleotides. Some stabilizers act on the polynucleotides and some act on the vesicles. Some stabilizers provide chemical stability and others increase structural stability. Multiple different types of stabilizers may be used together. Chemicals such as salts, chelators, or sugars can stabilize the polynucleotide molecules themselves. These or similar nucleic-acid stabilizers may be added during the formation of the vesicles. Protective layers may also be used to encapsulate the vesicles. The protective layers can encapsulate the vesicles in a protective shell.

One type of suitable protective coating is silica. Silica, also known as silicon dioxide, has the chemical formula $SiO_2$ and is the major constituent of many types of sand and is the primary ingredient in glass. Silica encapsulation may be performed by exposing the vesicles to a tetra alkoxysilane such as tetraethyl orthosilicate (TEOS). Encapsulation in silica can hermetically seal the vesicles under glass thereby further protecting the polynucleotides from chemical attack, high temperatures, and humidity. Storage conditions may be selected to further enhance longevity of the polynucleotides. For example, the polynucleotides in self-assembling vesicles may be stored at cool temperatures with low humidity such as, for example, 9° C. and 20% relative humidity. When encased in silica and stored under favorable conditions, the polynucleotides may be preserved without significant degradation for hundreds, thousands, or potentially millions of years.

Following storage, which may be for tens or hundreds of years, any protective layer may be removed from the vesicles with an etching solution that dissolves the protective layer without harming the polynucleotides. For silica encapsulating layers, buffered hydrogen fluoride is a suitable etching solution. If dried, the vesicles are rehydrated and the polynucleotides are released from the vesicles by lysing or disrupting the self-assembling membrane. Once returned to solution, the polynucleotides may then be sequenced or otherwise processed. When the polynucleotides are used for data storage, the sequence of nucleotide bases in the polynucleotides may be decoded to obtain the stored digital information.

These structures and techniques described in this disclosure have applications for storing synthetic polynucleotides encoding digital information but are equally suitable for storing naturally occurring polynucleotides.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter. The term "techniques," for instance, may refer to system(s) and/or method(s) as permitted by the context described above and throughout the document.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Polynucleotides such as DNA and ribonucleic acid (RNA), including polynucleotides that have unnatural bases, may be used to store digital information by designing a sequence of nucleotide bases that encodes the zeros and ones of the digital information. There are various techniques and encoding schemes known to those of skill in the art for using nucleotide bases to represent digital information. See e.g., Grass et al., *Robust Chemical Preservation of Digital Information on DNA in Silica with Error-Correcting Codes*, 54 Angew. Chem. Int. Ed. 2552 (2015) and Organick et al., *Random access in large-scale DNA data storage*, 36:3 Nat. Biotech. 243 (2018). Advantages of using DNA rather than another storage media for storing digital information include information density and longevity. The DNA storage structure and methods described in this disclosure can improve both information density and longevity relative to other techniques for storing DNA. The contents of the disclosure may be used with any type of polynucleotide such as DNA, RNA, and DNA-RNA hybrids; thus, references to "DNA" are illustrative and not intended to limit the application to only DNA or to only use of natural nucleotide bases.

There are many types of damage that can occur to polynucleotides such as hydrolytic damage, oxidative damage, radiation damage, and chemical damage. Hydrolytic damage is caused by the presence of water including humidity in the air and involves deamination or the total removal of individual bases. Polynucleotides stored in water may be subject to breakdown through enzymatic degradation pathways and also by depurination. Depurination is a chemical reaction of purine deoxyribonucleosides, deoxyadenosine and deoxyguanosine, and ribonucleosides, adenosine or guanosine, in which the β-N-glycosidic bond is hydrolytically cleaved releasing a nucleic base, adenine or guanine, respectively. When depurination occurs with DNA, it leads to the formation of AP (apurinic/apyrimidinic) sites that are unstable and promote strand cleavage. Hydrolytic damage is one of the major sources of damage to polynucleotides during storage.

Oxidative damage caused by reactive oxygen species (ROS) is another major source of damage for stored polynucleotides. ROS are chemically reactive chemical species containing oxygen. Examples include peroxides, superoxide, hydroxyl radical, singlet oxygen, and alpha-oxygen. Exposure to ROS results in oxidation of DNA strands through the deoxyribose sugar and most prominently to bases with unstable bonds, fragmentation, and cross-coupling. Oxidative DNA damage occurs most readily at guanine residues due to the high oxidation potential of this base relative to cytosine, thymine, and adenine. 8-hydroxy-deoxyguanosine (8-OHdG) is the most common marker for oxidative DNA damage. High temperature increases the chances of strand fragmentation as well as complete pyrolysis.

Ultraviolet and other types of radiation such as cosmic radiation (e.g., proton or neutron damage) can damage polynucleotides through free-radical mechanisms such as strand breaks and cross-linking. Fragmentation or strand breaks involve a cut in one or both DNA or RNA strands. Radiation-induced damage can also result in the production of pyrimidine dimers, where covalent cross-links occur in cytosine and thymine residues. These premutagenic lesions alter the structure and possibly the base-pairing. The most common pyrimidine dimers are cyclobutane pyrimidine dimers (CPD) and pyrimidine (6-4) pyrimidone photoproducts (6-4PP).

Chemical DNA damage may result from exposure to polycyclic aromatic hydrocarbons (PAHs). PAHs are potent, ubiquitous atmospheric pollutants commonly associated with oil, coal, cigarette smoke, and automobile exhaust fumes. A common marker for DNA damage due to PAHs is Benzo(a)pyrene diol epoxide (BPDE). BPDE is found to be very reactive and known to bind covalently to proteins, lipids, and guanine residues of DNA to produce BPDE adducts.

Cold storage methods can reduce the damage that polynucleotides accumulate while in storage, but the use of refrigerators, freezers, and liquid nitrogen is expensive and inefficient. Room-temperature storage reduces reliance on bulky and expensive equipment to control temperature. One technique for storing DNA at room temperature is by placement of liquid samples on filter paper cards (e.g., Whatman® FTA® cards) with chemicals that lyse cells and stabilize nucleic acids. Another room-temperature storage technique referred to as DNAshell® and RNAshell® (Imagene) places purified and desiccated polynucleotides under an inert gas such as nitrogen, helium, or argon inside airtight, stainless steel capsules. Additionally, there is a recently developed technique for adsorbing nucleotides to carbon-functionalized magnetic nanoparticles (e.g., TurboBeads®) and encapsulating the nanoparticles in silica as described in U.S. Pat. No. 11,059,016 entitled "Silica Encapsulated DNA on Magnetic Nanoparticles" filed on Jun. 25, 2018. However, all of the room-temperature techniques described above rely on a physical substrate or container that adds substantial volume and reduces the maximum density of polynucleotide storage. Filter paper, stainless steel capsules, nanoparticles, all contribute their own volume thus using space in storage that could otherwise be occupied by polynucleotides. This cost to storage density is inherent in any storage system that uses containers or substrates.

Stably storing polynucleotides reduces the extent and rate to which these and other types of damage occur. The term "stably storing" refers to storage conditions that preserve the items stored in an unchanged or substantially unchanged condition for a period of time longer than the item would be unchanged absent the specific storage conditions. In the context of polynucleotide storage, "stably storing" may refer to storing polynucleotide at room temperature and relative humidity of approximately 50% for greater than 10 years with less than 1% degradation. "Stably storing" may also refer to a technique or structure for storage that reduces degradation of the items stored to a rate that is less than half that of items stored under similar conditions without the use of the specific storage technique or structure.

Figure 1:
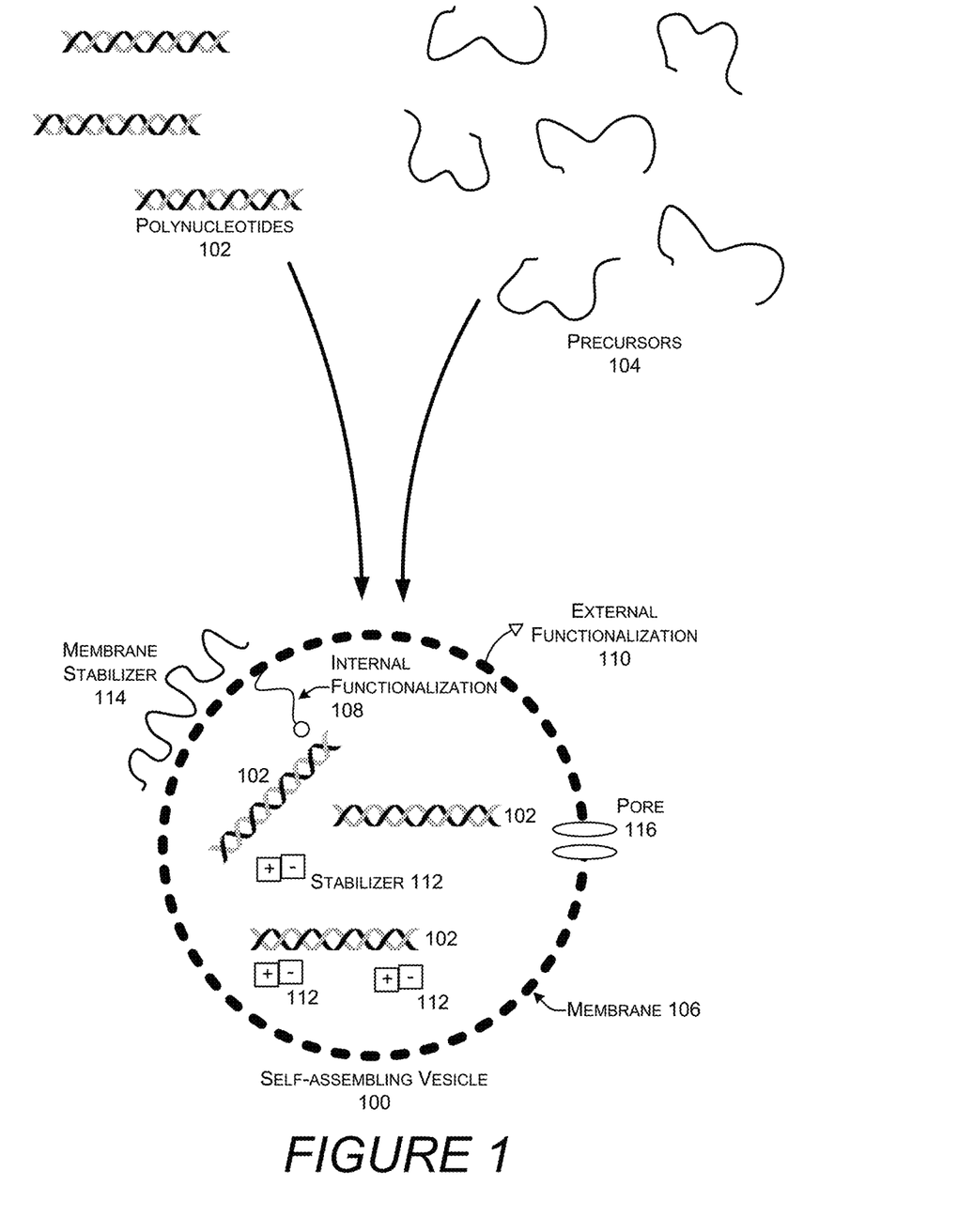
FIG. 1 is a diagram illustrating mixing of polynucleotides and vesicle precursors to form a self-assembling vesicle that contains the polynucleotides.

FIG. 1 illustrates a schematic representation of a self-assembling vesicle 100 that may contain polynucleotides 102 and other components. The self-assembling vesicle 100 is generally spherical in shape and is created from aggregation of precursors 104 into a membrane 106. The polynucleotides 102 may be DNA, RNA, single-stranded (ss), double-stranded (ds), DNA-RNA hybrids, and/or include unnatural bases. The length of the polynucleotides 102 may be, but is not limited to, approximately 80-300 base pairs (bp), approximately 100-200 bp, approximately 120-180 bp, or approximately 150 bp. The polynucleotides 102 may encode digital information. The self-assembling vesicle 100 may be a protocell, a liposome, a micelle, a colloidosome, a proteinosome, coacervate, or another type of vesicle with a biological membrane. The precursors 104 are capable of self-assembling to form the membrane 106 of the self-assembling vesicle 100. The specific type of precursor 104 depends on the type of vesicle 100 and may be native biological lipids, modified lipids, polyamines, polycations, synthetic organic polymers, and/or a combination thereof.

Many of the types of vesicles covered within the scope of this disclosure may be referred to as "protocells." Protocells are self-organized, endogenously ordered, spherical collections of lipids that include some functions similar to natural biologic cells. Lipids that form protocells are amphipathic molecules that have both hydrophilic and lipophilic properties. Phospholipids are one type of amphiphilic molecule and are the main components of biological membranes.

Liposomes, a type of protocell, are spherical vessels with an aqueous core and at least one lipid bilayer. Liposomes are most often composed of phospholipids, especially phosphatidylcholine, but may also include other lipids, such as egg phosphatidylethanolamine, so long as they are compatible with lipid bilayer structure. Liposomes may be multilamellar consisting of several concentric bilayers, separated by aqueous compartments or unilamellar, consisting of only one phospholipid bilayer surrounding one aqueous compartment.

Micelles are another type of spherical protocell that differs from liposomes due to the lack of an aqueous core. A micelle is an aggregate (or supramolecular assembly) of surfactant molecules dispersed in a liquid colloid. A typical micelle in aqueous solution spontaneously forms an aggregate with the hydrophilic "head" regions in contact with surrounding solvent, sequestering the hydrophobic single-tail regions in the micelle center.

A colloidosome is a microcapsule with a shell that consists of coagulated or fused colloid particles. To qualify as a colloid, the mixture must be one that does not settle or would take a very long time to settle appreciably. The dispersed-phase particles have a diameter between approximately 1-1000 nm. Colloidosomes may be created as Pickering emulsions which an emulsion is stabilized by the addition of solid particles such as colloidal silica.

Proteinosomes are a type of protein-based spherical capsules that have a semi-permeable, stimulus-responsive, enzymatically active, elastic membrane consisting of a closely packed monolayer of conjugated, amphiphilic protein-polymer building blocks. Formation is by self-assembly of a supramolecular protein-polymer conjugate. One protein-polymer conjugate that may be used to form protinosomes is βCD-modified bovine serum albumin (BSA) and adamantane-terminated poly(N-isopropylamide) (Ad-PNI-PAM) in aqueous solution. Another suitable protein-polymer conjugate is an aqueous solution of cationized bovine serum albumin ($BSA-NH_2$)-poly(N-isopropylacrylamide) (PNI-PAAm) nanoconjugates. This results in a Pickering emulsion where the amphiphilic BSA-PNIPAAm conjugates self-assemble at the interface forming emulsion droplets. A Pickering emulsion is an emulsion that is stabilized by solid particles which adsorb onto the interface between two phases. Chemical cross-linking such as with PEGbis(N-succinimidyl succinate) can provide additional structural stability. Proteinosomes can be dispersed in oil or water, thermally cycled to temperatures of 70° C., and partially dried and re-inflated without loss of structural integrity.

Coacervates are spherical aggregates of cationic and anionic water-soluble polymers that interact in water to form liquid, polymer-rich colloidal droplets held together by hydrophobic forces. Coacervate droplets can measure from 1-100 μm across, while their soluble precursors are typically on the order of less than 200 nm.

All the types of vesicles described above have the characteristic of forming substantially instantaneously in solution when the appropriate precursors 104 are mixed together in the desired ratios under the appropriate conditions such as pH and salt concentration. Additionally, when appropriate precursors 104 are mixed with polynucleotides 102, formation of the vesicles selectively encapsulates the polynucleotides 102 resulting in a polynucleotide 102 concentration within the self-assembling vesicle 100 that is higher than the concentration of the polynucleotides 102 in the surrounding solution. Encapsulation of polynucleotides 102 may be promoted by forming the self-assembling vesicles 100 with a polynucleotide-attracting material encased inside. For example, the vesicles with aqueous cores may be formed in the presence of streptavidin with oil so that the hydrophilic streptavidin preferentially remains in the aqueous interior. Biotinylated polynucleotides 102 may diffuse through the membrane 106 and anchor to the encapsulated streptavidin.

The polynucleotides 102 and precursors 104 may be mixed manually or by using any suitable type of automated liquid-handling equipment such as an automatic pipetting robot or microfluidics system using any type of suitable technique for moving liquids such as channel-based microfluidics, digital microfluidics, acoustic droplet ejection (ADE), or other techniques. In an implementation, a first fluid channel containing the precursors 104 may be mixed with a second fluid channel that supplies the polynucleotides 102. The polynucleotides 102 may be provided in an aqueous solution such as an annealing buffer at a concentration of, for example, around 20, 30, 40, 50, 60, 70, 80, 90, or 100 μg/mL. The polynucleotides 102 provided to the second fluid channel may be the polynucleotides 102 encoding a particular digital file. Thus, dispensing of the polynucleotides 102 through the automated liquid-handling equipment may be done on a file-by-file basis or otherwise divided according to the information content of the polynucleotides 102.

The self-assembling vesicle 100 may be modified with internal functionalization 108 and/or external functionalization 110 on the internal surface or the surface of the external self-assembling vesicle 100. The internal functionalization 108 may include the addition of functional groups that attract the polynucleotides 102. For example, internal functionalization 108 may include a direct targeting mechanism such as streptavidin attracting biotinylated polynucleotides 102. The polynucleotides 102 are readily biotinylated in the course of oligonucleotide synthesis by the phosphoramidite method using commercial biotin phosphoramidite. Other high-affinity binding complexes besides streptavidin-biotin may also be used.

Electrostatic charge may be used to attract the polynucleotides 102 to the interior of the self-assembling vesicle 100. The internal functionalization 108 may add a polycationic molecule to the interior of the membrane 106 that attracts negatively charged polynucleotides 102. The polycationic molecule may be a polycationic linear macromolecule such as polyethyleneimine (PEI), poly-L-lysine (PLL), diethylaminoethyl-dextran (DEAE-dextran), or a branched polymer such as poly(amidoamine) (PAMAM) dendrimers.

PEI or polyaziridine is a polymer with repeating unit composed of the amine group and two-carbon aliphatic $CH_2CH_2$ spacer. Linear polyethyleneimines contain all secondary amines. PLL is a specific chiral configuration of the synthetic polymer α-polylysine with 1-lysine at lysine's central carbon. DEAE-dextran is a positively charged dextran derivative that binds and interacts with negatively-charged DNA molecules and via an unknown mechanism. PAMAM is a class of dendrimer that is made of repetitively branched subunits of amide and amine functionality. PAMAMs have a sphere-like shape overall and are typified by an internal molecular architecture including tree-like branching, with each outward layer, or generation, containing exponentially more branching points. Surface amine residues on PAMAM dendrimers bind to the phosphate backbone of DNA through charged interactions.

Additionally, short oligonucleotide fragments (e.g., ssDNA and/or ssRNA) attached to the interior of the self-assembling vesicle 100 may provide sequence-specific attraction for particular polynucleotides 102 due to strand hybridization. The internal functionalization 108 may add a nucleic acid sequence to the inside of the membrane 106 that is complementary to the nucleic acid sequence at one of the ends of the polynucleotides 102. For example, if the polynucleotides 102 are designed with primer binding sites at one or both ends, then the primer sequence may be used for the internal functionalization 108 to selectively attract those polynucleotides 102 having the primer binding site. Synthetic polynucleotides 102 such as those used for storing digital information will have known sequences and may include intentionally designed to include primer binding sites that are specific to the type of information encoded. Thus, the internal functionalization 108 may cause the self-assembling vesicle 100 to selectively uptake only a selective subset of the polynucleotides 102 available in solution and this subset may be only those polynucleotides 102 encoding a specific type of information (e.g., a particular computer file).

External functionalization 110 adds functional groups to the outside of the membrane 106. The external functional groups may be the same or different than the internal functionalization 108. For example, the external functionalization 110 may attract polynucleotides 102 to the exterior surface of the self-assembling vesicle 100. External functionalization 110 may also create a covalent bond or non-covalent interaction with an encapsulating layer (shown in FIG. 2) that surrounds the self-assembling vesicle 100.

External groups may also control the pore size of the membrane 106 and block large polynucleotides 102 from entering. For example, large external groups may create steric hindrance that prevents polynucleotides above a certain length from entering a membrane pore. Thus, in this way, external functionalization 110 can act as a size-exclusion gate. Size-specific access to pores may also be controlled by using external groups that can undergo conformational modifications. For example, click chemistry modifiers that cross-link under specific conditions such as addition of a metal catalyst (e.g., copper(I)-catalyzed azide/alkyne cycloaddition (CuAAC)).

One or more types of stabilizers may be associated with the self-assembling vesicle 100. One type of stabilizer is a nucleic-acid stabilizer 112 that stabilizes the polynucleotides 102 inside the self-assembling vesicle 100. The nucleic-acid stabilizer 112 may be a salt such as a chloride salt (e.g., sodium chloride, calcium chloride, magnesium chloride, lanthanum chloride, etc.) a phosphate salt (e.g., calcium phosphate), a nitrate (e.g., calcium nitrate, magnesium nitrate, lanthanum nitrate, etc.), a carbonate (e.g., calcium carbonate, magnesium carbonate, lanthanum carbonate, etc.), sodium benzoate, magnesium sulfate, lanthanum bromide, or a mixture thereof. Cations in the salt may be selected from the group comprising calcium, magnesium, and lanthanum. Anions in the salt may be selected from the group comprising chloride, fluoride, nitride, bromide, iodide, phosphate, carbonate, nitrate, perchlorate, iodate, and bromate. Chelators such as ethylenediaminetetraacetic acid (EDTA) and diaminocyclohexane tetraacetate are another type of suitable nucleic-acid stabilizer 112. Additionally, polysaccharides such as dextran, raffinose, and trehalose can function as nucleic-acid stabilizers 112. Nucleic acids may also be stabilized by sugar alcohols such as mannitol and polyamines such as spermine. Furthermore, commercially available chemical stabilizers such as GenTegra™-DNA available from GenTegra® LLC and DNAstable® available from Biomatrica® may also be used as the nucleic-acid stabilizer 112.

A membrane stabilizer 114 may be used to stabilize the membrane 106 of the self-assembling vesicle 100. The membrane stabilizer 114 may be a small molecule such as a radical scavenger that protects the self-assembling vesicle 100 from ultraviolet radiation and/or peroxides. Protective molecules that may be used as the membrane stabilizer 114 include butylated hydroxytoluene ("BHT" which is a lipophilic organic compound, a derivative of phenol), diphenylamine (an organic compound with the formula $(C_6H_5)_2NH$), phosphite esters (organophosphorus compounds with the formula $P(OR)_3$), benzophenone (a UV-blocking organic compound with the formula $([phenyl]C_6H_5)_2CO$, abbreviated $Ph_2CO$), and the like.

The precursors 104 may also contain components that form pores 116 in the self-assembling vesicle 100. Pores 116 may be formed from a number of different natural or synthetic molecules such as alpha-haemolysin, DNA origami nanopores, cyclodextrin, gramicidin, and calixarene. Many biological pores or synthetic channels will spontaneously embed in the membrane 106 during formation of the self-assembling vesicle 100.

The pores 116 may also be formed by electroporation. Electroporation forms temporary pores in the membrane 106 as a result of applying an electrical field that increases membrane permeability. Electroporation works by passing thousands of volts across a distance of one to two millimeters through a solution of suspended vesicles. Subjecting the membrane 106 to a high-voltage electric field results in temporary breakdown creating pores 116 that are large enough to allow polynucleotides to enter or leave the self-assembling vesicle 100.

Passage of polynucleotides into and out of the self-assembling vesicle 100 may also be regulated by controlling membrane permeability. Even in the absence of pores 116, the membrane 106 may allow macromolecules (e.g., polynucleotides) to pass through. A combination of precursors that react through a "click chemistry" reaction may also be used to change membrane permeability and selectively adjust the size of molecules that can pass through the membrane 106. A click chemistry reaction is one that is wide in scope and easy to perform, uses only readily available reagents, and is insensitive to the presence of oxygen and water.

Molecules that participate in click chemistry reactions may be included in the membrane 106 and selectively activated to change membrane permeability. In general, greater cross linking among the molecules present in the membrane 106 decreases membrane permeability and decreases the length of polynucleotides that may pass through. Thus, the extent of membrane cross linking can function as a size-specific filter for polynucleotide uptake. For example, alkynes like cyclooctyne combine with azides to undergo azide-alkyne Huisgen cycloaddition due to strain. The ratio of the precursors can control the extent of cross linking and size of molecule that can pass through membrane 106. Copper-catalyzed click chemistry reactions (e.g., CuAAC) can be controlled by the length of time the reactions are allowed to proceed. Longer reaction time generally results in the membrane becoming less permeable and lowering the threshold size of molecules that can enter.

Additional protection may be achieved by forming multiple vesicle membranes around the polynucleotides 102. After the self-assembling vesicle 100 is formed, additional precursors for a different type of vesicle may be added and these precursors may form a second membrane (not shown) around the existing membrane 106. For example, liposomes may be encapsulated in proteinosomes to create a double membrane of two different vesicle types around the polynucleotides 102. Additional layers, e.g., a third layer of coacervate membrane, may also be added. Recall that the external functionalization 110 may add functional groups that attract polynucleotides 102. Polynucleotides 102 attached or attracted to the exterior of the membrane 106 may be encapsulated by a second vesicle membrane to create alternating layers of vesicle membranes and polynucleotides 102. This may be repeated for vesicles with more than two membrane layers.

Figure 2:
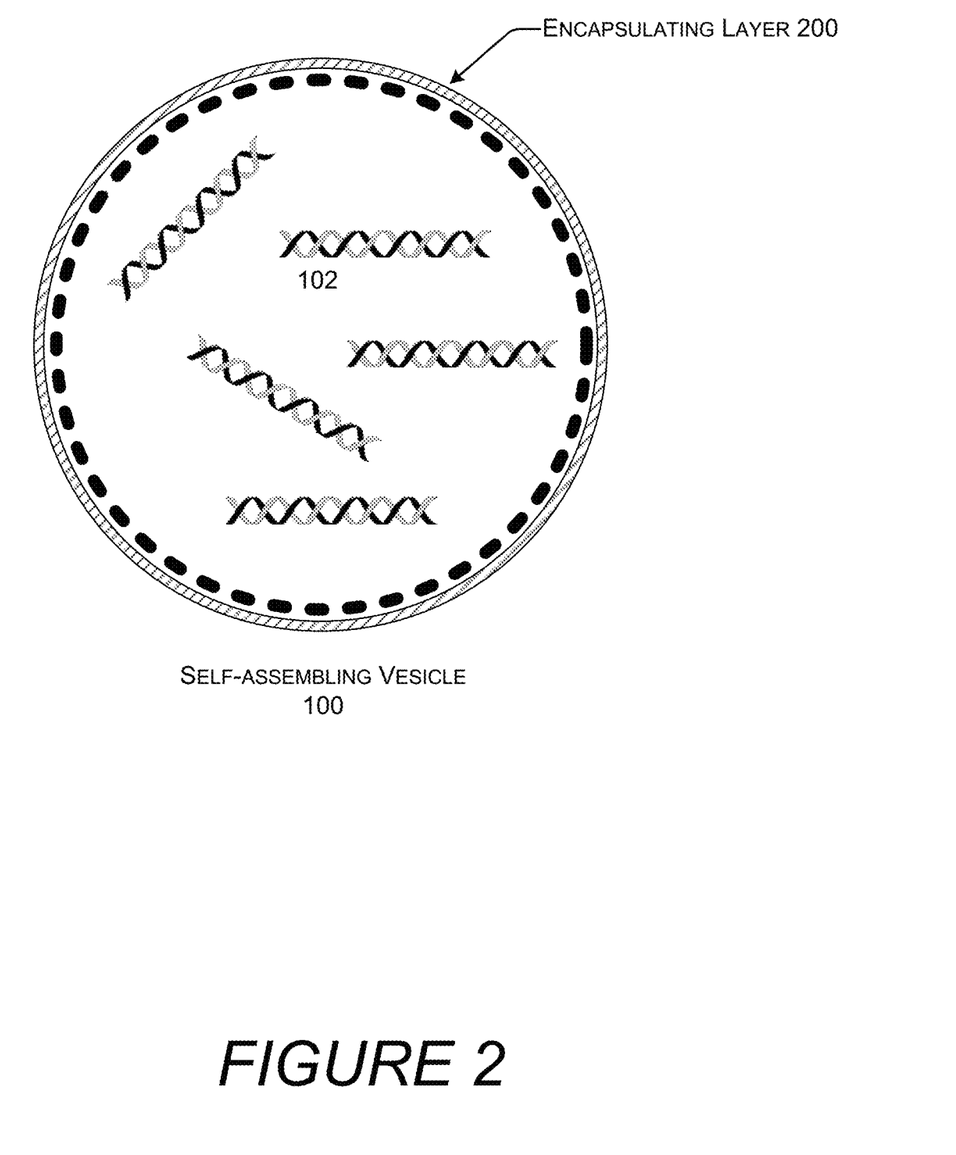
FIG. 2 is a diagram showing the self-assembling vesicle of FIG. 1 surrounded by an encapsulating layer.

FIG. 2 shows the self-assembling vesicle 100 surrounded by an encapsulating layer 200. The encapsulating layer 200 is not an additional self-assembling membrane as described above, but is a structural, protective layer formed from a non-reactive material such as silica, titanium, gold, a thin film wax (e.g. lipid), cyanate-derived ester resins, biocompatible and biodegradable polysaccharide hydrogels such as those made from chitosan-tripolyphosphate, nanocellulose composites, fibroin (i.e., silk protein) or other polymeric or monomeric molecule. The types of polymers that may be used in the encapsulating layer 200 include polyester-based polymers, diblock co-polymers, and tri-block co-polymers. Specific examples of suitable polymers include polylactic acid (PLA), polyethylene glycol (PEG), PEG-PDLLA, PEG-PLA, Poly(methyl methacrylate) (PMMA), poly(N-(2-hydroxypropyl)methacrylamide) (HPMA), or poly(lactic-co-glycolic acid) (PLGA). Metals such as titanium or gold can provide a thin film around the self-assembling vesicle 100 that prevents entry of damaging chemicals, light, and moisture. Multiple encapsulating layers (not shown) such as a layer of silica further surrounded by layer titanium are also possible.

Silica, also known as, silicon dioxide, silicic acid, or silicic acid anhydride is an oxide of silicon with the chemical formula $SiO_2$. Encapsulation in silica can hermetically seal the polynucleotides 102 under glass thereby protecting them from ROS, chemical attack, high temperatures, and humidity. An encapsulating layer 200 made of silica may be formed by contacting the self-assembling vesicle 100 with a silica-containing compound such as one or more tetra alkoxysilanes. In an implementation, the tetra alkoxysilane(s) may have an alkoxy chain with between one and five carbon atoms. For example, the tetra alkoxysilane may be tetramethyl orthosilicate, tetraethyl orthosilicate (TEOS), tetrapropyl orthosilicate, tetrabutyl orthosilicate, tetrapentyl orthosilicate, or mixtures thereof. TEOS is the most prevalent alkoxide of silicon. It is a chemical compound with the formula $Si(OC_2H_5)_4$. TEOS is a colorless liquid that degrades in water. TEOS is the ethyl ester of orthosilicic acid, $Si(OH)_4$. TEOS easily converts to silicon dioxide upon the addition of water. This hydrolysis reaction is an example of a sol-gel process. The side product is ethanol. The reaction proceeds via a series of condensation reactions that convert the TEOS molecule into a mineral-like solid via the formation of Si—O—Si linkages. Rates of this conversion are sensitive to the presence of acids and bases, both of which serve as catalysts.

The silica-containing compound may be in an aqueous solution and mixed with dried self-assembling vesicles 100 for an extended period of time such as several hours or days. The mixing may be facilitated by use of a shaker. In an implementation, the mixing may be performed for 12 hours, 24 hours, 48 hours, 72 hours, 96 hours, or longer. Longer periods of mixing may result in a thicker silica shell forming around the self-assembling vesicle 100. In some implementations, the silica layer formed over the self-assembling vesicles 100 by this method may be approximately 10 nm thick.

An encapsulating layer 200 of silica may also be formed by sputter deposition of silicon dioxide. Sputter deposition is a physical vapor deposition (PVD) method of depositing thin films by ejecting sputtering material from a "target" that is a source of the material, then depositing it onto a "substrate" which in this application would be the self-assembling vesicles 100. Chemical vapor deposition (CVD) may also be used to deposit silica onto the self-assembling vesicles 100. CVD is a deposition method used to apply a thin film of solid material to a surface typically under vacuum. For example, with CVD, polycrystalline silicon may be deposited from trichlorosilane ($SiHCl_3$) or silane ($SiH_4$).

Additionally or alternatively, titanium dioxide, $TiO_2$, or gold may be deposited on the self-assembling vesicle 100 by CVD, for example, by low-pressure CVD (LPCVD) which is CVD at sub-atmospheric pressures. Titanium dioxide can form a thin film over the self-assembling vesicle 100 which may have a thickness of about 15 nm.

External functionalization on the surface of the self-assembling vesicle 100 may form covalent bonds to the material that makes up the encapsulating layer 200. The covalent bond may strengthen the association between that encapsulating layer 200 and the self-assembling vesicle 100. Additionally, during retrieval of the polynucleotides, removal of the encapsulating layer 200 will also remove fragments of the membrane due to the covalent bond. This may increase the ease of purifying the polynucleotides when retrieved from storage.

As a form of additional protection or as an alternative to encapsulating the self-assembling vesicles 100, the self-assembling vesicles 100 may be covered with a thin film. The thin film may be a plastic film made of synthetic organic polymers such as polyethylene plastic wrap or plastic paraffin film. The self-assembling vesicles 100 may be dried to prevent trapping moisture under the thin film. Covering the self-assembling vesicles 100 with a thin film does not surround and encapsulate the entirety of the vesicles with the thin film, but rather covers one side of the self-assembling vesicles while the other side is protected by a substrate or support material on which the self-assembling vesicles 100 are placed.

Illustrative Processes

For ease of understanding, the processes discussed in this disclosure are delineated as separate operations represented as independent blocks. However, these separately delineated operations should not be construed as necessarily order dependent in their performance. The order in which the process is described is not intended to be construed as a limitation, and any number of the described process blocks may be combined in any order to implement the process or an alternate process. Moreover, it is also possible that one or more of the provided operations is modified or omitted.

Figure 3:
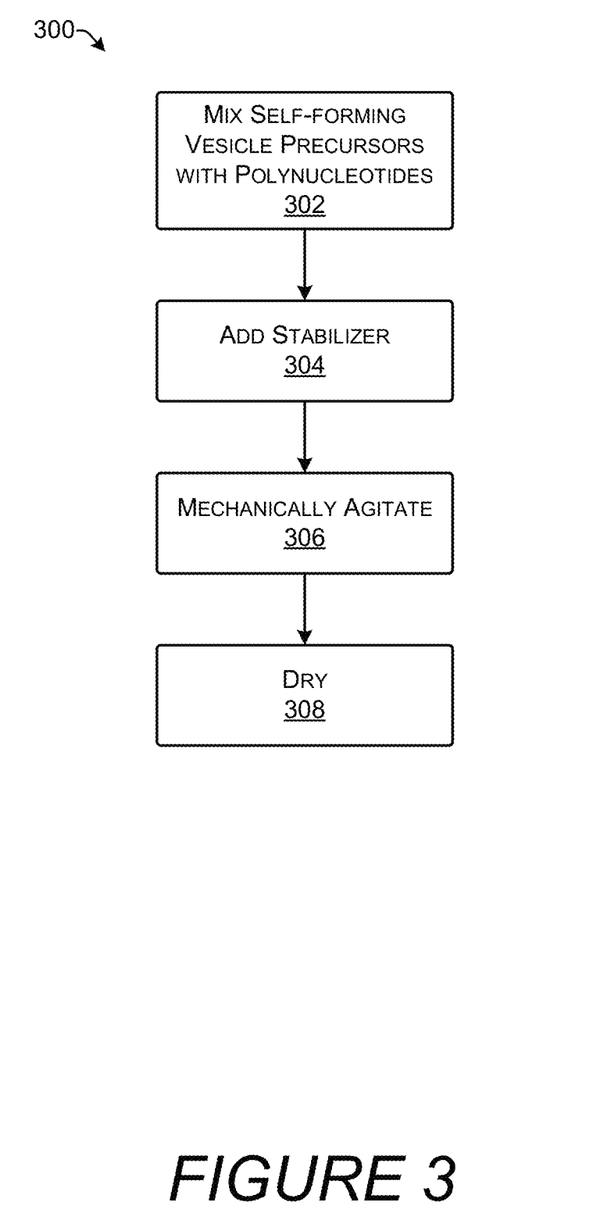
FIG. 3 flow diagram showing an illustrative process for storing polynucleotides in self-assembling vesicles.

FIG. 3 shows process 300 for storing polynucleotides in self-assembling vesicles. Process 300 may be implemented using the structures shown in FIGS. 1 and 2.

At operation 302, self-assembling vesicle precursors are mixed with a solution of polynucleotides. The mixing may be performed manually or by use of automated liquid-handling equipment. The self-assembling vesicle precursors may be amphipathic lipids such as phospholipids, colloid particles, conjugated protein-polymers such as BSA-PNI-PAAm, oppositely charged macroions, polyesters, polysaccharides, or the like. The polynucleotides may be in a solution of annealing buffer (e.g., at a concentration of 50 µg/ml). The annealing buffer may be any standard buffering solution for polynucleotides such as 400 mM Tris-HCl, 500 mM NaCl, and 100 mM $MgCl_2$. The polynucleotides may have a length of about 100-300 bp such as a length of approximately 150 bp. In an implementation, the polynucleotides may encode digital information.

At operation 304, one or more stabilizers are added. The stabilizers may be nucleic-acid stabilizers that stabilize the polynucleotides, membrane stabilizers that stabilize the membranes of the self-assembling vesicles, and an encapsulating layer that contacts the outside of the self-assembling vesicles. The nucleic-acid stabilizer may be any type of known stabilizer for DNA or RNA such as salts, chelators, polysaccharides, polyamines, or commercial stabilizer formulations. The membrane stabilizers may be any type of molecular structure that stabilizes the membrane of the vesicles. The particular membrane stabilizer will vary with the type of vesicle. The encapsulating layer may be formed from a non-reactive material such as silica, titanium, or a polymer. Any number of different types of stabilizers may be combined. For example, the polynucleotides may be stabilized with a nucleic-acid stabilizer and the self-assembling vesicle may be stabilized with membrane stabilizers and surrounded by an encapsulating layer.

At operation 306, the mixture of polynucleotides, self-assembling vesicle precursors, and stabilizers are mechanically agitated. Mechanical agitation may be performed by vortexing, sonication, or other means. Mechanic agitation may increase the speed of vesicle formation. DNA or RNA shearing due to vortexing or sonication is unlikely when the length of the polynucleotide strands is relatively short (i.e., <500 bp) as is the case for artificially synthesized polynucleotides. Mild heat (e.g., about 60-80° C.) may also be used to increase the rate of vesicle formation.

At operation 308, the self-assembling vesicles are dried. Addition of salts as nucleic-acid stabilizers may enhance desiccation of the vesicles and polynucleotides contained within. The dry vesicles may take the form of a powder that can be transferred to one or more containers, spotted on a flat surface, or otherwise manipulated in powder form. Spotting onto a flat surface may be used to place portions of the dried vesicles at known, addressable locations that can be later identified based on the position of the spotting on the flat surface. Alternatively, spotting may be performed while the vesicles are still wet and then they may be dried after.

Any suitable drying technique may be used. In an implementation, drying may be performed by use of a centrifugal evaporator or vacuum centrifuge. A centrifugal evaporator includes a vacuum pump connected to a centrifuge chamber in which samples are placed. The system works by lowering the pressure in the centrifuge system insert—as the pressure drops so does the boiling point of the solvent(s) in the system. When the pressure is sufficiently low that the boiling points of the solvents are below the temperature of the sample holder, then they boil. This enables solvent to be rapidly removed while the samples themselves are not heated to damaging temperatures. The samples may be processed at room temperature or heated in the centrifugal evaporator to around 25-50° C. Spray drying is another technique that is suitable for drying the self-assembling vesicles. Spray drying is the process of converting a mixture in its liquid form to a powder. This is done by removing the moisture component from the liquid solution. The solution, sometimes called an emulsion, is sprayed through a nozzle into a chamber that simultaneously has hot air being blown into it. Drying may also be performed by lyophilization ("freeze drying").

Figure 4:
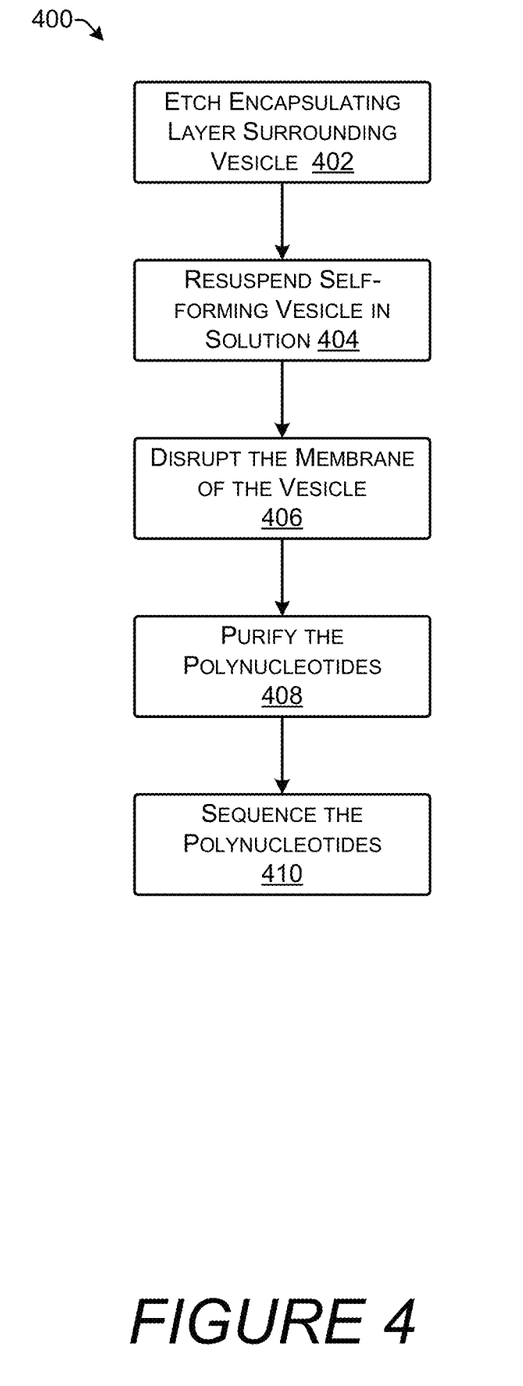
FIG. 4 is a flow diagram showing an illustrative process for retrieving polynucleotides that are stored in self-assembling vesicles.

FIG. 4 shows process 400 for obtaining polynucleotides stored in vesicles with self-assembling membranes that are protected by an encapsulating layer.

At operation 402, the protective encapsulating layer surrounding the self-assembling vesicle is etched. The technique used for removing the encapsulating layer depends on the materials used in the encapsulating layer. Silica or metal encapsulating layers can be removed by etching. The etching may be performed by contacting the self-assembling vesicle with an etching solution. The specific etching solution will be selected based on the type of encapsulating layer. Removing the encapsulating layer will expose the self-assembling vesicle.

Silica dissolves rapidly in fluoride-containing solutions (forming $SiF_6^{2-}$). Thus, an etching buffer containing fluoride may be used to dissolve the silica. The compatibility of dilute etching solutions and DNA (DNA is not affected by $F^-$ ions) has previously been shown. The etching buffer may be a mixture of a buffering agent such as ammonium fluoride ($NH_4F$) and hydrofluoric acid (HF). In an implementation, the etching buffer may be prepared by dissolving 0.23 g of ammonium hydrogen difluoride ($NH_4FHF$, puriss, Sigma-Aldrich, cat. no. 30101) in 5 mL of $H_2O$ and 0.19 g of $NH_4F$ (puriss, Sigma-Aldrich, cat. no. 30101) in 5 mL of $H_2O$ then mixing the two solutions together. Thus, a buffered hydrogen fluoride solution is one suitable etching solution.

A titanium encapsulating layer may also be etched with hydrogen fluoride. For example, an etching solution for titanium may be made from 9 V/V % hydrofluoric acid, 12 V/V % nitric acid, and distilled water. A gold encapsulating layer may be etched with potassium cyanide (KCN).

Etching of the protective encapsulating layer may be performed by shaking the self-assembling vesicle in the presence of the etching solution. In an implementation, the shaking may be performed for approximately two minutes at about 900 RPM. No matter how performed, etching may be followed by a washing or cleaning step in which the etched material and etching solution are removed.

At operation 404, the self-assembling vesicle is resuspended in solution. The solution may be in an aqueous solution such as a buffered solution. It may be the same solution that the self-assembling vesicle precursors were stored in prior to vesicle formation.

At operation 406, the membrane of the self-assembling vesicle is disrupted. The specific technique used for disrupting the membrane will depend on the type of vesicle. Many biological membranes that can be used to form vesicles may be disrupted with ultrasonication. Ultrasonification uses high-frequency ultrasound (18 kHz-1 MHz) caused by rapid sinusoidal movement of a probe within a liquid. Ultrasonication produces cavitation phenomena when acoustic power inputs are sufficiently high to allow the production of multiple microbubbles at nucleation sites in the fluid. The bubbles grow during the rarefying phase of the sound wave, then are collapsed during the compression phase. On collapse, a violent shock wave passes through the medium. The whole process of gas bubble nucleation, growth, and collapse due to the action of intense sound waves is called cavitation. The collapse of the bubbles converts sonic energy into mechanical energy in the form of shock waves equivalent to several thousand atmospheres (300 MPa) pressure. This energy imparts motions to the membrane of the self-assembling vesicle which disintegrates.

Besides ultrasonification, enzymes or other chemicals may be used to disrupt the membrane of the self-assembling vesicle. The membranes of some types of self-assembling vesicles may be disrupted by the addition of enzymes such as esterases or lipases that hydrolyzes the membrane components. An esterase is a hydrolase enzyme that splits esters into an acid and an alcohol in a chemical reaction with water called hydrolysis. A lipase is any enzyme that catalyzes the hydrolysis of fats (lipids). Lipases are a subclass of the esterases. Non-enzyme chemicals that degrade the membrane components may also be used to disrupt some self-assembling vesicles. The specific enzyme or chemical used can be selected based on the composition of the vesicle membrane.

At operation 408, the polynucleotides are purified from the remnants of the encapsulating layer, the physical membrane, and other material in solution. Purification removes remnants such as silica, membrane fragments, salts, stabilizers, and other compounds from the solution leaving "clean" polynucleotides that are ready for further processing. If the encapsulating layer is covalently bound to the membrane through external functional groups that were present on the self-assembly vesicle, then etching the protective layer at 402 may also remove the remnants of the membrane.

If the polynucleotides are bound to internal functional groups on the membrane of the self-assembling vesicle, purification may include disrupting this association to separate the polynucleotides from the membrane fragments. A release solution may be used to release the polynucleotides from internal functional groups such as, for example, by displacing the polynucleotides. For example, if the internal functional groups are polycationic molecules that form electrostatic attachment to the polynucleotides, the release solution may include poly(acrylic acid) sodium (PAS) which is a polyanionic molecule that displaces the polynucleotides. This release solution may be made by diluting 40 mg of PAS in 50 mL of ultrapure water to a concentration of 0.8 mg/mL and mixing that with sodium chloride diluted in ultrapure water until saturation at room temperature in a ratio of PAS:NaCl=20:80. As used herein, "ultrapure water" refers to water having a purity such that resistivity is 18.2 MΩ·cm at 25° C. or "type 1" water as specified in ISO (International Organization for Standards) 3696. One source of ultrapure water is Milli-Q™ water available from Millipore Corporation.

Other techniques for separating the polynucleotides from internal functional groups may be used depending on the type of functional group. For example, if the internal functionalization is streptavidin, short incubation in an aqueous solution above 70° C. will break the interaction between biotinylated polynucleotides and streptavidin allowing for purification of the polynucleotides.

Many techniques for purifying DNA are known to those of ordinary skill in the art. For example, phenol-chloroform extraction followed by ethanol precipitation, ethanol precipitation alone, silica column-based kit such as the QIAquick PCR purification kit (Qiagen, cat. no. 28104), anion exchange, magnetic beads that bind polynucleotides in a pH-dependent manner, or other technique.

At 410, the polynucleotides are sequenced. The polynucleotides may be sequenced with any sequencing technology such as sequencing-by-synthesis or Nanopore sequencing. Prior to sequencing, the polynucleotides may be amplified by polymerase chain reaction (PCR) which increases the amount of DNA available. If the polynucleotides encode digital information, the nucleotide base sequence obtained from sequencing the polynucleotides may be decoded to recover the digital information.

EXAMPLES

In the following examples, the "sample DNA" was a 150 bp double-stranded DNA molecule with an arbitrary sequence. The sample DNA was obtained from Integrated DNA Technologies (IDT), PCR amplified and purified using standard techniques. In these examples, every copy of the sample DNA had the same sequence, but in an actual implementation for storage of digital information there would be many different sequences represented in a pool of DNA molecules.

Figure 5:
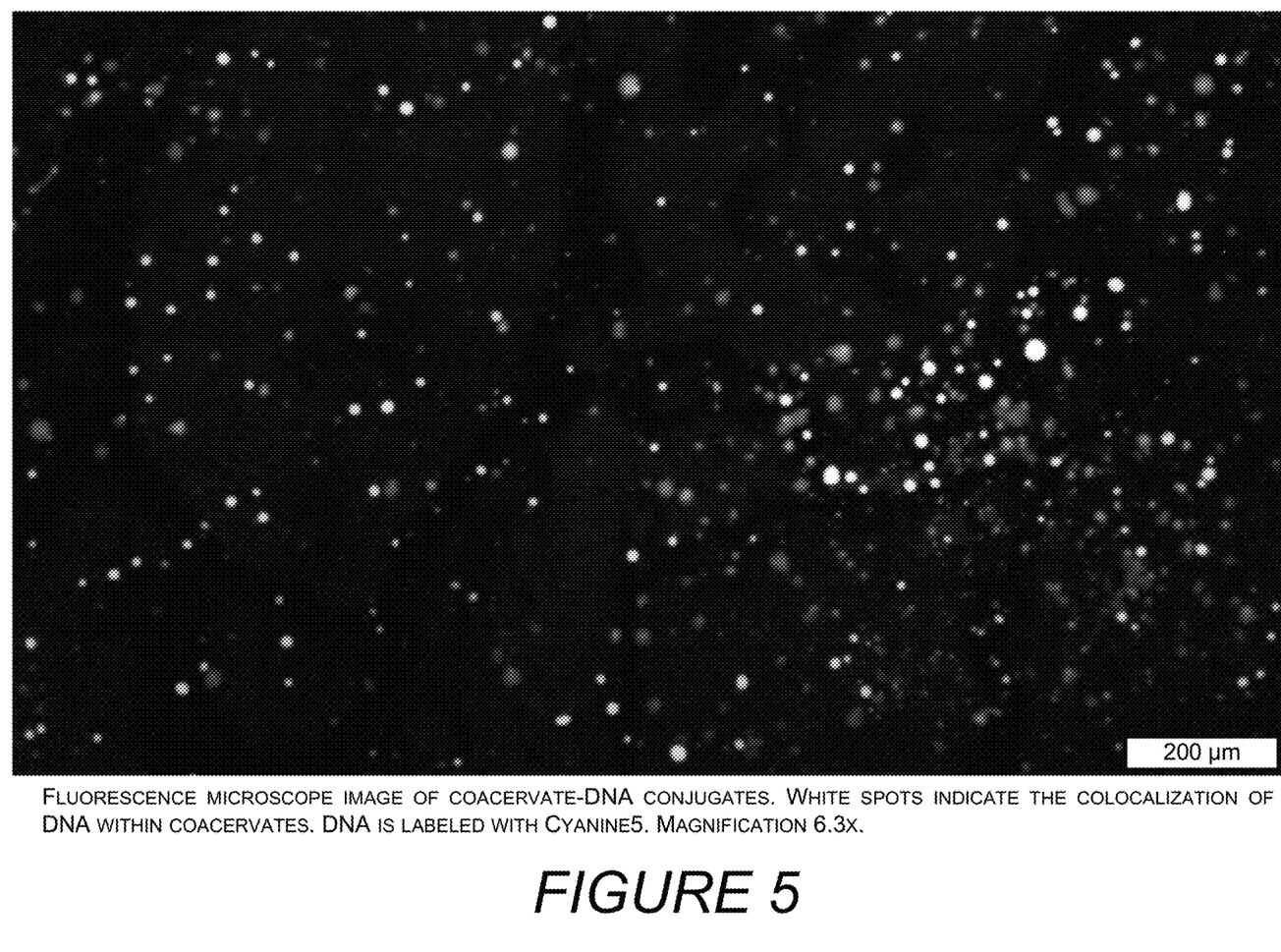
FIG. 5 is a fluorescence microscope image of coacervate-DNA conjugates.

FIG. 5 is a fluorescence microscope image of coacervate-DNA conjugates. The white or light-colored spots on the image indicate colocalization of the DNA within the coacervates. The coacervates were formed from a mixture of poly-T oligonucleotides (ssDNA molecules with approximately 20 thymine bases) and poly-L-lysine (poly K) both obtained from IDT. The sample DNA was fluorescently labeled on its 5' end with 0.5 µL of a 100 µM stock cyanine 5 (Cy5)-labeled oligonucleotide. Cy5 is a fluorescent dye that belongs to the Cyanine family of synthetic polymethine dyes. Cy5 is reactive, water-soluble, and has an absorbance maximum of 649 nm and an emission maximum of 670 nm.

First, 9 µL of 1 mM poly-T was mixed with the sample DNA. This oligonucleotide mixture was vortexed briefly. Next, 1 µL of 10 mM of poly-L-lysine was added to the oligonucleotide mixture to form coacervates. This mixture was again vortexed to promote coacervate formation. The coacervates were visualized on an Olympus BX53M microscope equipped with a Cy5™ Filter Cube Set (available from Edmund Optics® stock #67-010-OLY) showing that the sample DNA is concentrated in the spherical coacervates.

Figure 6:
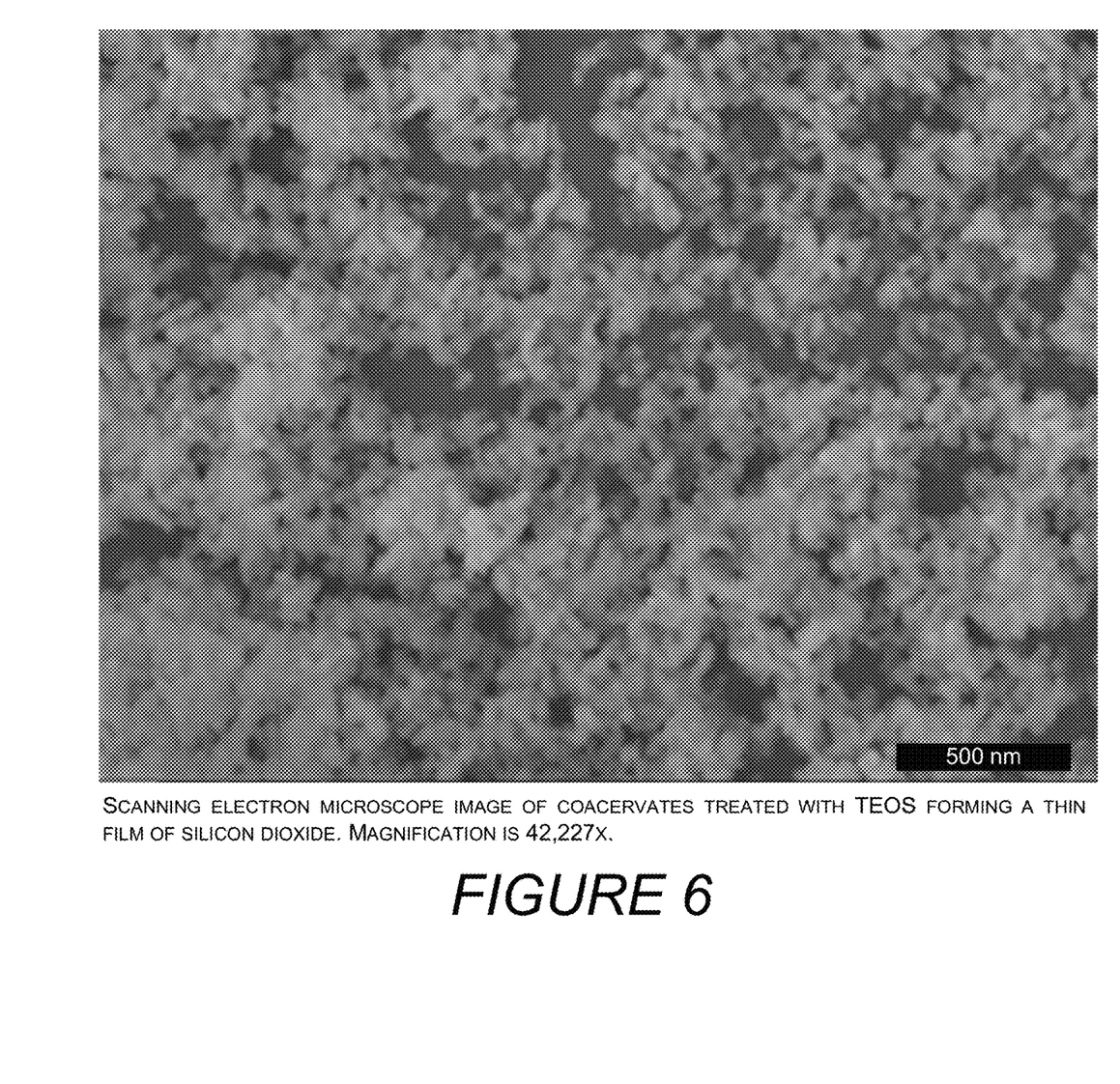
FIG. 6 is a scanning electron microscope (SEM) image of coacervates covered with a thin film of silicon dioxide.

FIG. 6 is a scanning electron microscope (SEM) image of coacervates encapsulated in silicon dioxide. The coacervates were created by mixing 89.1 µL of 1 mM poly-T, 9.9 µL of 10 mM poly-L-lysine, and 4.95 µL of the sample DNA followed by vortexing. The sample DNA was labeled with fluorescein amidite (FAM). FAM is a synthetic equivalent of fluorescein dye. Thirty L of this mixture was diluted in 470 µL of DNase and RNase free molecular grade water. To provide silica encapsulation, 4.5 µL of reagent grade 98% TEOS solution (Sigma-Aldrich, catalog number 131903) was added to the diluted coacervate mixture. The TEOS was allowed to react with the coacervates for four days at room temperature with shaking at 900 rpm. The SEM image generated by a Sirion XL30 scanning electron microscope shows silica-encapsulated coacervates. The silica-encapsulated coacervates are both smaller and appear to have more uniform sizing than the coacervates shown in FIG. 5.

Figure 7:
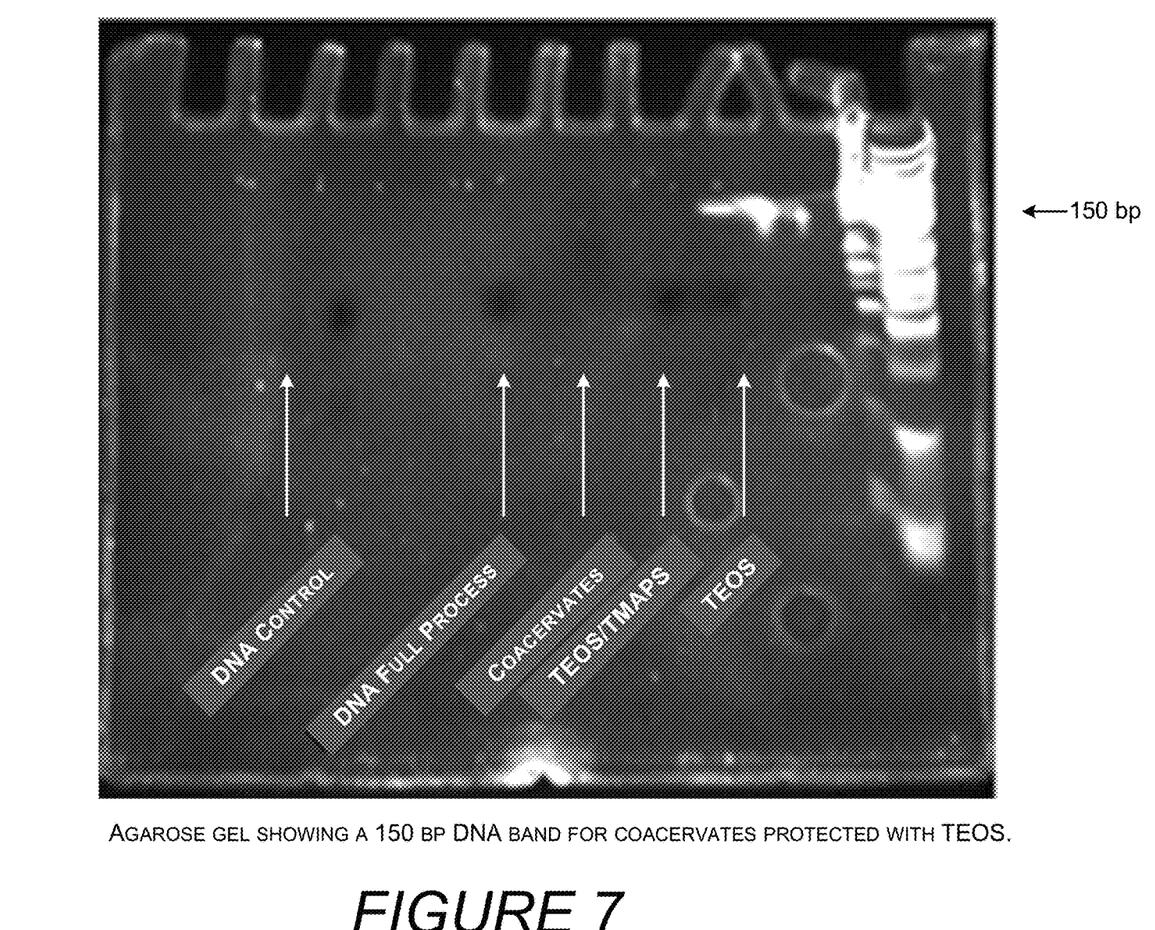
FIG. 7 is an image of an electrophoretic gel showing that encapsulation with silica protects DNA from degradation by reactive oxygen species (ROS).

FIG. 7 is an image of an electrophoretic gel showing that encapsulation of coacervates with TEOS protects from degradation by bleach. The DNA control is the 150 bp sample DNA without any processing or protection. DNA full process is DNA prepared without addition of the coacervate precursors, TEOS, or tris-(methoxy)aminopropylsilane (TMAPS). The coacervates sample is coacervates containing the sample DNA without any additional protective layer. The coacervates sample was prepared using the procedure described for FIG. 6 but without addition of TEOS. The TEOS/TMAPS sample was also prepared using the procedure of FIG. 6 with the modification of including 0.5 µL of 50% 3-(trimethylammonium) propylfunctionalized silica (TMAPS) solution in ethanol during the four days of shaking. TMAPS is an abbreviation for N-Trimethoxysilylpropyl-N,N,N-trimethylammonium. The chloride salt of TMAPS has the formula $C_9H_{24}ClNO_3Si$ and is available in 50% methanol from Fisher Scientific company L.L.C. (catalog number AAH6641414). The TEOS sample was prepared according to the procedure described for FIG. 6.

All samples were exposed to a 5% bleach solution for 30 minutes. Bleach is known to degrade DNA and is a source of strong reactive oxygen species (ROS). All samples other than the DNA control were etched for approximately five minutes with 50 µL of a hydrofluoric acid etching solution prepared by dissolving 0.23 g of ammonium hydrogen difluoride ($NH_4FHF$, puriss, Sigma-Aldrich, catalog number 30101) in 5 mL of $H_2O$ and 0.19 g of $NH_4F$ (puriss, Sigma-Aldrich, catalog number 30101) in 5 mL of $H_2O$ then mixing the two solutions together. The DNA from all samples other than the DNA control were cleaned by mixing with 50 µL of 0.3 M NaOAc to remove the poly-L-lysine that formed the coacervates.

All samples were run on an electrophoretic gel. Only the sample of coacervates encapsulated in TEOS had a band at 150 bp. DNA in the other samples was apparently fully degraded by exposure to bleach. Without being bound by theory, it is believed that the combination of TEOS and TMAPS forms a different crystal structure than TEOS alone and that the TEOS/TMAPS crystal structure provides less protection.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. An article of manufacture for storing polynucleotides comprising: a self-assembling vesicle containing polynucleotides; and a stabilizer.

Clause 2. The article of manufacture of clause 1, wherein the self-assembling vesicle is a protocell, a liposome, a micelle, a colloidosome, a proteinosome, or a coacervate.

Clause 3. The article of manufacture of clause 1 or 2, wherein the self-assembling vesicle further comprises pores that exclude polynucleotides above a threshold size.

Clause 4. The article of manufacture of clause 1-3, wherein an internal surface of the self-assembling vesicle is functionalized with functional groups that attract the polynucleotides.

Clause 5. The article of manufacture of clause 4, wherein the functional groups comprise a nucleic acid sequence complementary to a portion of a sequence of the polynucleotides.

Clause 6. The article of manufacture of clause 1-5, wherein the polynucleotides are present in the self-assembling vesicle at a higher concentration than in a solution containing the polynucleotides prior to formation of the self-assembling vesicle.

Clause 7. The article of manufacture of clause 1-6, wherein the stabilizer is a nucleic-acid stabilizer present inside the self-assembling vesicle.

Clause 8. The article of manufacture of clause 7, wherein the nucleic-acid stabilizer comprises at least one of sodium benzoate, a chloride salt, a phosphate salt, ethylenediaminetetraacetic acid (EDTA), diaminocyclohexane tetraacetate, dextran, raffinose, trehalose, mannitol, or spermine.

Clause 9. The article of manufacture of clause 1-8, wherein the stabilizer is an encapsulating layer contacting the outside of the self-assembling vesicle.

Clause 10. The article of manufacture of clause 9, wherein the encapsulating layer comprises silicon dioxide, titanium dioxide, gold, a thin-film wax, an ester resin, a polysaccharide hydrogel, PEG, PLA, PEG-PDLLA, PEG-PLA, PMMA, HPMA, PLGA, chitosan-tripolyphosphate, nanocellulose composites, or silk fibroin.

Clause 11. The article of manufacture of clause 9, wherein an exterior of the self-assembling vesicle is functionalized to covalently bond with the encapsulating layer.

Clause 12. A method for concentrating and stably storing polynucleotides comprising: mixing self-assembling vesicle precursors with a solution containing the polynucleotides; and adding a stabilizer, wherein a first concentration of the polynucleotides inside a vesicle formed from the self-assembling vesicle precursors is higher than a second concentration of the polynucleotides in the solution.

Clause 13. The method of clause 12, wherein the self-assembling vesicle precursors are amphipathic lipids, colloid particles, conjugated protein-polymers, oppositely charged macroions, polyesters, or polysaccharides.

Clause 14. The method of clause 12 or 13, wherein the stabilizer is a nucleic-acid stabilizer that associates with and stabilizes the polynucleotides, a membrane stabilizer that associates with and stabilizes an external surface of the vesicle, or a protective structural layer that encapsulates the vesicle.

Clause 15. The method of clause 12-14, further comprising mechanically agitating a mixture of the self-assembling vesicle precursors and the solution containing polynucleotides.

Clause 16. The method of clause 12-15, further comprising drying the vesicle containing the polynucleotides.

Clause 17. A method of accessing polynucleotides stored in a self-assembling vesicle comprising: etching a protective encapsulating layer surrounding the self-assembling vesicle to expose the self-assembling vesicle; resuspending the self-assembling vesicle in solution; disrupting a membrane of the self-assembling vesicle; and purifying the polynucleotides.

Clause 18. The method of clause 17, wherein etching the protective encapsulating layer comprises contacting the self-assembling vesicle with a hydrogen fluoride solution.

Clause 19. The method of clause 17 or 18, wherein disrupting the membrane comprises ultrasonication, contacting the membrane with a hydrolase, or contacting with membrane with a chemical that degrades one or more membrane components.

Clause 20. The method of clause 17-19, further comprising sequencing the polynucleotides and decoding a sequence of nucleotide bases obtained from the sequencing to recover digital information stored in the polynucleotides.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention (especially in the context of the following claims) are to be construed to cover both the singular and the plural, unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context. The terms "portion," "part," or similar referents are to be construed as meaning at least a portion or part of the whole including up to the entire noun referenced. As used herein, "approximately" or "about" or similar referents denote a range of ±10% of the stated value.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents and/or patent applications (collectively "references") throughout this specification. Each of the cited references is individually incorporated herein by reference for its particular cited teachings as well as for all that they disclose.

The invention claimed is:

1. A method for concentrating and stably storing polynucleotides comprising:
   synthesizing the polynucleotides to have sequences according to an encoding scheme that encodes digital information in a sequence of nucleotide bases of the polynucleotides;
   mixing self-assembling vesicle precursors with a solution containing the polynucleotides;
   adding a stabilizer, wherein the polynucleotides, the self-assembling vesicle precursors, and the stabilizer form a self-assembling vesicle containing the polynucleotides;
   drying the self-assembling vesicle until substantially all moisture is removed;
   storing the self-assembling vesicle at room temperature; and
   forming a protective encapsulating layer surrounding the self-assembling vesicle, wherein the protective encapsulating layer comprises silicon dioxide or titanium dioxide.

2. The method of claim 1, wherein the self-assembling vesicle precursors are amphipathic lipids, colloid particles, conjugated protein-polymers, oppositely charged macroions, polyesters, or polysaccharides.

3. The method of claim 1, wherein the stabilizer is a nucleic-acid stabilizer that associates with and stabilizes the polynucleotides, or a membrane stabilizer that associates with and stabilizes an external surface of the vesicle.

4. The method of claim 3, wherein the stabilizer is the nucleic-acid stabilizer and the nucleic-acid stabilizer comprises at least one of a salt, a chelator, a polysaccharide, or a sugar alcohol.

5. The method of claim 1, further comprising mechanically agitating a mixture of the self-assembling vesicle precursors and the solution containing polynucleotides.

6. The method of claim 1, further comprising:
   etching the protective encapsulating layer surrounding the self-assembling vesicle to expose the self-assembling vesicle;
   resuspending the self-assembling vesicle in solution;
   disrupting a membrane of the self-assembling vesicle; and
   purifying the polynucleotides.

7. The method of claim 6, wherein etching the protective encapsulating layer comprises contacting the self-assembling vesicle with a hydrogen fluoride solution.

8. The method of claim 6, wherein disrupting the membrane comprises ultrasonication, contacting the membrane with a hydrolase, or contacting with membrane with a chemical that degrades one or more membrane components.

9. The method of claim 6, further comprising sequencing the polynucleotides and decoding a sequence of nucleotide bases obtained from the sequencing to recover digital information stored in the polynucleotides.

10. The method of claim 1, wherein drying the vesicle containing the polynucleotides until substantially all moisture is removed comprises drying the vesicle to a powder.

11. The method of claim 1, further comprising adding functional groups, wherein the functional groups functionalize the internal surface of the vesicle and attract the polynucleotides such that a first concentration of the polynucleotides inside the vesicle formed from the self-assembling vesicle precursors is higher than a second concentration of the polynucleotides in the solution.

12. The method of claim 1, wherein the stabilizer is a protective structural layer that encapsulates the vesicle.

* * * * *